United States Patent [19]

Whitbourne et al.

[11] Patent Number: 5,069,899
[45] Date of Patent: Dec. 3, 1991

[54] ANTI-THROMBOGENIC, ANTI-MICROBIAL COMPOSITIONS CONTAINING HEPARIN

[75] Inventors: Richard J. Whitbourne, Fairport; Margaret A. Mangan, Rochester, both of N.Y.

[73] Assignee: Sterilization Technical Services, Inc., Rochester, N.Y.

[21] Appl. No.: 430,340

[22] Filed: Nov. 2, 1989

[51] Int. Cl.$^5$ .................. A61K 31/74; A61K 37/547; A61K 31/725; A01N 37/18

[52] U.S. Cl. .................................. 424/56; 424/94.64; 514/2; 514/12; 514/196; 514/197; 514/201; 514/209; 530/830; 536/21; 523/112

[58] Field of Search ...................... 424/94.64, 101, 78; 514/2, 12, 56; 530/830; 536/21; 523/112

[56] References Cited

U.S. PATENT DOCUMENTS

| | | | |
|---|---|---|---|
| 3,844,989 | 10/1974 | Harumiya et al. | 260/17.4 |
| 4,119,094 | 10/1978 | Micklus et al. | 128/132 R |
| 4,239,664 | 12/1980 | Teng et al. | 514/56 |
| 4,326,532 | 4/1982 | Hammar | 514/56 |
| 4,442,133 | 4/1984 | Greco et al. | 427/2 |
| 4,713,402 | 12/1987 | Solomon | 514/56 |
| 4,871,357 | 10/1989 | Hsu et al. | 514/56 |

OTHER PUBLICATIONS

Gott, V. L., J. D. Whiffen & R. C. Dutton: Heparin Bonding on Colloidal Graphite Surfaces-Science 1.12:1297, 1963.

Gott, V. L., J. D. Whiffen, D. E. Koepke, R. L Daggert, W. C. Boake & W. P. Yang, Techniques of Applying a Graphite-Benzal Kanium-Heparin Coating to Various Plastics & Metals, Trans. Amer. Svc. Artif. Intern. Organs. 10:213, 1964.

Grade G. A., S. J. Anderson, H. M. Giotta & R. D. Falb: Non-Thrombogenic Materials via a Simple Coating Process: Trans. Amer. Soc. Artif. Ioter Organs 15:1, 1969.

Amplatz, K.: A Simple Non-Thrombogenic Coating Invest. Ratl. Jul.-Aug., 1971, vol. 6, pp. 280-289.

Primary Examiner—Thurman K. Page
Assistant Examiner—Carlos Azpuru
Attorney, Agent, or Firm—Marjama & Pincelli

[57] ABSTRACT

Anti-thrombobenic, anti-microbial compositions containing heparin reacted with quaternary ammonium components and bound with water-insoluble polymers are disclosed. Such compositions may also contain additional quaternary ammonium compounds not reacted with heparin and may also contain quaternary ammonium compound(s) reacted with antibiotics.

11 Claims, No Drawings

ANTI-THROMBOGENIC, ANTI-MICROBIAL COMPOSITIONS CONTAINING HEPARIN

BACKGROUND OF THE INVENTION

Many kinds of polymer compositions have been used in the field of medical supplies. These compositions have not always exhibited anti-thrombogenic characteristics when used in prosthetic and therapeutic apparatuses for handling or being in contact with blood or blood components under conditions where clotting would tend to occur, such as artificial blood vessels, catheters, artificial hearts, and artificial kidneys.

When blood is brought in contact with metal, glass, plastic or other similar surfaces, it tends to clot in a short time unless certain precautions are taken. One common precaution currently in widespread use is the treatment of the surface with heparin or with heparin reacted with quaternary ammonium compounds. Such heparin compounds are known to have anti-coagulant effects when in contact with blood. The presence of the aforementioned heparin compounds on the surface imparts anti-thrombogenic characteristics. However, previously known heparinization or compositions have not been adequate because of the short time of anti-thrombogenic activity, at most a few days in vivo (I. S. Hersch, et al, J. Biomed., Mater. Res. Symposium I, 99–104 (1971); K. Amplatz, "A simple Non-Thrombogenic Coating", Invest. Radiology, July, August, 1971, Vol. 6 or because the anti-thrombogenic characteristic was reduced to a very low level in order to make it resistant to removal by reacting it with quaternary ammonium polymers (U.S. Pat. No. 3,844,989).

It is therefore, an object of the present invention to provide novel anti-thrombogenic polymer/heparin compound compositions or mixtures which prevent blood clotting for a relatively long period of time (over one month), and which have the same high degree of anti-thrombogenic characteristics as the non-polymerized heparin-quaternary ammonium compounds, and thus provide excellent properties for use as medical materials for coatings on artificial blood vessels, catheters, artificial hearts, artificial kidneys, etc.

Another object of the present invention is to provide novel anti-microbial surfaces which contain antibiotic agents which are entrained in the surface in such a way as to be gradually released in vivo to provide effective anti-microbial action over a longer time than was previously possible when using these agents. Typical agents useful in this embodiment of the invention include penicillins, cephalosporins, etc.

SUMMARY OF THE INVENTION

The anti-thrombogenic, anti-microbial compositions (mixtures) of this invention comprise heparin-quaternary ammonium compounds mixed with water-insoluble polymers. They may also contain some hydrophilic polymers, but the mixture would still be water-insoluble after coating and drying. The water-insoluble polymers of this invention range from hydrophobic polymers to ones that are fairly hydrophilic, but are nevertheless essentially water-insoluble after being coated on a substrate and dried. A single polymer or mixture(s) of different polymers may be used to accomplish the invention. The heparin-quaternary ammonium compound may be mixed in a solution with the water-insoluble polymer, or it may be coated on top of a coating of the water-insoluble polymer(s), which is applied to the surface beforehand. In the latter case, a solvent must be added that is a mutual solvent for both the heparin-quaternary ammonium compound and the water-insoluble polymer(s) so that some mixing occurs between the two layers. In still another case, it is possible to coat the heparin-quaternary ammonium compound directly on the water-insoluble plastic surface, and incorporate a mutual solvent for both the plastic surface and the heparin-quaternary ammonium compound, so that some mixing occurs between the plastic surface and the heparin-quaternary ammonium compound.

Various combinations of these three systems would be obvious to one skilled in the art. The mixtures of the water-insoluble polymer(s) and heparin-quaternary ammonium compounds of this invention are substantially more resistant to removal or deactivation in human and animal body fluids such as blood or plasma than the heparin-quaternary ammonium compounds by themselves.

Typical examples of polymers suitable for use with the present invention are as follows: Water insoluble cellulose esters such as cellulose acetate, cellulose acetate butyrate, cellulose acetate propionate, and cellulose nitrate; polyurethane resins including polyether and polyester grades. Exemplary of the polyurethane is the reaction product of 2,4-tolylene diisocyanate and position isomers thereof, 4,4'-diphenylmethane diisocyanate and position isomers thereof, polymethylenepolyphenyl isocyanate, or 1,5-napthylene diisocyanate with 1,2-polypropylene glycol, polytetramethylene ether glycol, 1,4-butanediol, 1,4-butylene glycol, 1,3-butylene glycol, poly(1,4-oxybutylene)glycol, caprolactone, adipic acid esters, phthalic anhydride, ethylene glycol, 1,3-butylene glycol, 1,4-butylene glycol or diethylene glycol. Acrylic polymers such as ethyl and methyl acrylate and methacrylate; condensation polymers such as those produced by sulfonamides such as toluenesulfonamide and aldehydes such as formaldehyde; and polyisocyanates. Exemplary of the polyisocyanate are polymethylenepolyphenyl isocyanate, 4,4'-diphenylmethane diisocyanate and position isomers thereof, 2,4-tolylene diisocyanate and position isomers thereof, 3,4-dichlorophenyl diisocyanate and isoferrone isocyanate. Adducts or prepolymers of isocyanates and polyols such as the adduct of trimethylolpropane and diphenylmethane diisocyanate or tolylene diisocyanate are suitable. For further examples of polyisocyanates, see "Encyclopedia of Polymer Science and Technology", H. F. Mark, N. G. Gaylord and N. M. Bikales (eds.) (1969) incorporated herein by reference.

Typical quaternary ammonium compounds that can be reacted with heparin for use in this invention include benzalkonium chloride, tridodecylmethylammonium chloride, cetylpyrrdinium chloride, benzyldimethylstearylammonium chloride, benzylcetyldimethylammonium chloride, etc.

DETAILED DESCRIPTION OF THE INVENTION

The compositions of the present invention are first dissolved in solvent mixtures that are co-solvents for the mixtures of non-volatile components and which allow compatible homogenous films of the components to be cast. Such films when dried will typically appear as a clear film or films of very slight turbidity indicating that the non-volatile components have been deposited in a substantially homogenous manner. Typical solvents comprise alcohols, ketones, esters, aromatics, pyrrollidones, carboxylic acids, amides, and other organic solvents used alone or in appropriate mixtures as required, and which bring about the basic compatibility of the non-volatile components to be expressed. Typical surfaces which can be coated include plastic, metal and glass.

The heparin-quaternary ammonium compounds may be prepared in the conventional manner by any known prior art technique. For example, a heparin-benzalkonium chloride compound can be prepared by mixing approximately equal volumes of a 10% (by wt.) aqueous solution of sodium heparin with an approximately 17% (by wt.) solution of benzalkonium chloride (i.e., Zephiran from Winthrop-Breon Laboratories), and then washing the residual sodium chloride out with distilled or deionized water. Such preparations are disclosed in "A Simple Non-Thrombogenic Coating", K. Amplatz, Invest., Radiology, July, August, 1971, Vol. 6, which is incorporated herein by reference. It should be understood, however, that the invention is not limited to the heparin-quaternary ammonium compounds cited in the above reference.

In most cases, all the components are incorporated into a single solution so that the surface treatment can be accomplished with a single application. However, the treatment can also be applied in two steps. For example, the water-insoluble polymer(s) can be applied in one application and the heparin-quaternary ammonium compound can be applied to the water-insoluble polymer. Some mutual solvent(s) for the water-insoluble polymer and heparin-quaternary ammonium compound that makes two components compatible should be included in the overcoat application to accomplish the objective of the invention. For example, dimethylacetamide (DMA) effectively accomplishes this objective as shown in Example 1. A variant on this approach would involve application of the water-insoluble polymer(s) followed by application of a solution containing some water-insoluble polymers and some heparin-quaternary ammonium compound. Some heparin-quaternary ammonium compounds may also be added to the first application. Typical concentrations of heparin-quaternary ammonium compound in the coating solutions range from about 0.1% to 20% by weight. Preferred concentrations range from 0.5% up to 4%. Use of higher concentrations of heparin-quaternary ammonium compounds in the solutions does not enhance performance and is therefore not very useful or desired. Lower concentrations than those disclosed above reduce the anti-thrombogenicity of the layers.

Typical concentrations of the water-insoluble polymers in the coating solution range from about 0.01% to 20% by weight. Preferred concentrations range from about 0.2% to 3%. Higher concentrations tend to mask the anti-thrombogenic characteristics of the layers. Lower concentrations tend to allow the layer to be extracted more easily. The composition of the final coating may have the heparin-quaternary compound present in a concentration of about 0.5 to 99.5 percent by weight with the balance of the composition comprising essentially the water-insoluble polymer.

ANTI-THROMBOGENICITY TEST

The following in vitro test was used to evaluate anti-thrombogenicity: 10 mm × 75 mm glass test tubes were charged with 0.5 gm of reconstituted human plasma which had been kept refrigerated since collection. The test tubes were equilibrated in a 37° C. incubator for 10–30 minutes. Next, 0.1 g of 0.10M $CaCl_2$ was added, and the test tube was manually swirled to achieve complete mixing. Immediately after swirling, 4½" long sections of 7 French tubing (either coated with one of the anti-thrombogenic systems of the present invention, or uncoated controls) were dropped into the plasma in each tube, taking care to ensure that the sample pieces were completely immersed in the plasma. The tubes were maintained in the 37° C. incubator and were checked for clotting at one minute intervals by removing them from the incubator and tilting them. Before clotting, the liquid flows in the test tube, but it gels and does not flow once it has clotted. Typical clotting times for plasma containing untreated polyurethane tubing range from six minutes to 15 minutes. Samples made according to this invention prevent clotting in this test. It was found that if the plasma did not clot after standing overnight, it would usually not clot for up to four weeks. Therefore, tests were usually discontinued if they had not clotted after standing overnight. Typical samples prepared by this invention did not clot when tested before plasma extraction, and retained their anti-clotting activity after 28 or more days of extraction in plasma. Devices coated with heparin-benzalkonium chloride or heparin-tridodecylmethylammonium chloride do not clot when tested before extraction in plasma, but lose their anti-thrombogenicity after plasma extraction of two hours or less. Heparinized quaternary polymers (HQP), such as those prepared according to U.S. Pat. No. 3,844,989 and used on catheters marked under the trademark ANTHRON by Toray Medical Co. Ltd., show only slight anti-thrombogenicity. For example, when tested against heparin-benzalkonium chloride (HBAC), the HBAC sample prevented clotting of the plasma overnight, while the control clotted in five minutes and the HQP sample clotted in seven minutes before plasma extraction, and showed no improvement in anti-thrombogenicity compared to the untreated polyurethane control after 12 hours of plasma extraction.

The following examples are intended to illustrate various preferred embodiments of the present invention.

EXAMPLE 1

Polyurethane 7 French tubing was coated with a solution containing the following ingredients and dried for 20 minutes at 65° C.

| Polyvinylpyrrolidone | .006 g |
| Isopropanol | 1.0 g |
| Nitrocellulose | 1.6 g |
| Ethylacetate | 1.2 g |
| Rosin ester | .5 g |
| Butylacetate | 4.8 g |
| Dimethylacetamide | 1.5 g |
| Ethyl-3-ethoxy propionate | 6.1 g |

The tubing was then overcoated with a solution containing the following ingredients and then dried for 20 minutes at 65° C.

| Isopropanol | 9.85 g |
| Dimethylacetamide | 1.00 g |
| Heparin benzalkonium chloride | .15 g |

This sample was compared to a sample of polyurethane tubing which was coated with heparin benzalkonium chloride (1.8% w/v in isopropanol) as follows. The samples were dipped in a Gentian Violet dye solution and then rinsed in hot running water. The sample coated with heparin-benzalkonium chloride (HBAC) in isopropanol lost most of the surface dye stain in less than 20 seconds, indicating that most of the HBAC had been washed off. The sample of the present invention that had the nitrocellulose undercoat and contained DMA in the HBAC overcoat, retained the dye stain much longer indicating that it is much more resistant to removal.

EXAMPLE 2

Polyurethane 7 French tubing was coated with a solution consisting of:

| | |
|---|---|
| Methylethylketone | 5.0 g |
| Heparin-benzalkonium chloride | 0.33 g |
| Isopropanol | 3.7 g |
| Ethyl-3-ethoxy propionate | .6 g |
| Butyl acetate | .5 g |
| ½ sec. nitrocellulose | .16 g |
| Ethyl acetate | .1 g |
| Rosin ester | .05 g |

The samples were dried at 75° C. for 30 minutes. Samples were then extracted in human plasma at 37° C. for 7, 10, 21, or 28 days and then tested for anti-clotting properties. The following results were obtained.

| Sample | Clotting time |
|---|---|
| Uncoated control | 12 minutes |
| Above sample, without extraction in plasma | Did Not Clot |
| Above sample, after 7 days extraction in plasma | Did Not Clot |
| Above sample, after 10 days extraction in plasma | Did Not Clot |
| Above sample, after 21 days extraction in plasma | 24 minutes |
| Above sample, after 28 days extraction in plasma | 20 minutes |

The above results show that the samples are still exhibiting effective anti-clotting activity on the device surface where it is most needed and that clots are unlikely to form on the treated surfaces, even after 28 days of extraction. This level of anti-clotting activity is stronger even after 28 days of plasma extraction than the anti-clotting levels achieved under these test conditions with surfaces treated according to the compositions taught by U.S. Pat. No. 3,844,989.

EXAMPLE 3

The following solution was coated on polyurethane 7 French tubing and dried at 75° C. for 20 minutes.

| | |
|---|---|
| Methylethylketone | 5 g |
| 8.3% heparin benzalkonium chloride in isopropanol | 5 g |
| Cellulose Acetate Butyrate - 3A solution* | 1.5 g |
| *3A solution | |
| Ethyl-3-ethoxy propionate | 30.3 g |
| Butylacetate | 24.2 g |
| Ethyl acetate | 6.1 g |
| Rosin ester | 1.5 g |
| Isopropanol | 3.5 g |
| ½ sec. Cellulose acetate butyrate | 8.0 g |

Coated samples were tested for anti-clotting activity, and also for resistance to removal by dying with Gentian Violet dye and then rinsing with hot running water.

The sample was compared to a coating of heparin benzalkonium chloride without any cellulose ester polymer additive.

Results: The sample did not clot in the clotting test. In the hot water rinse test, the heparin benzalkonium chloride coating without cellulose resin was completely removed in a few seconds. Hot water rinsing did not remove the above coating which contained cellulose acetate butyrate polymer.

EXAMPLE 4

Polyurethane 7 French tubing was coated as in Example 3 except that cellulose acetate butyrate was replaced with cellulose acetate propionate. The sample was tested for anti-clotting activity and resistance to removal in hot water. Results were comparable to those with Example 3.

EXAMPLE 5

Polyurethane 7 French tubing was coated with the following solution and dried at 80° C. for 20 minutes.

| | |
|---|---|
| Methylethylketone | 5 g |
| 8.3% heparin benzalkonium chloride in isopropanol | 4 g |
| Cellulose acetate propionate 5A solution* | 2 g |
| *5A solution | |
| Ethyl-3-ethoxy propionate | 30.3 g |
| Butylacetate | 24.2 g |
| Ethylacetate | 6.1 g |
| Rosin ester | 2.5 g |
| Isopropanol | 3.5 g |
| ½ sec. cellulose acetate propionate | 8.0 g |

The coated sample was extracted in plasma at 37° C. for four hours and tested for anti-microbial activity by pressing it into gelled Difco Plate Agar which was spiked with *Staphylococcus epidermidis* (ATCC 12228) and then incubated overnight at 32°–35° C. A sample of polyurethane tubing that was coated with heparin-benzalkonium chloride without cellulose polymer was extracted in plasma at 37° C. for four hours for comparison. The sample which contained cellulose acetate propionate (CAP) polymer showed a significant zone of inhibition while the sample made without CAP resin showed no zone of inhibition, demonstrating that the incorporation of cellulose ester polymer effectively increases resistance to removal of the coating when extracted in human plasma.

EXAMPLE 6

Example 5 was repeated, except that the solution contained 1.5 gm of 10.7% (wt. %) nitrocellulose solution in place of the 2.0 grams of 10.7% (wt. %) CAP solution. Samples of polyurethane tubing coated with this solution were extracted in plasma at 37° C. for four hours or 18 hours. They were then tested for anti-microbial activity using the same zone of inhibition test as used in Example 5. The tests showed zones of inhibition after both extraction intervals. The sample extracted for four hours has a larger zone of inhibition than the sample that was extracted for 18 hours.

EXAMPLE 7

The following solution was coated on polyurethane 7 French tubing and dried at 80° C. for 20 minutes. A control was made by coating a sample of the tubing with a 5% w/v solution of Tridodecylmethylammonium chloride (TDMAC).

| Methylethylketone | 5 g |
| --- | --- |
| 8.3% heparin benzalkonium chloride in isopropanol | 4 g |
| 7A solution* | 1.5 g |

*7A solution

| Ethyl-3-ethoxy propionate | 30.3 g |
| --- | --- |
| Butylacetate | 24.2 g |
| Ethyl acetate | 6.1 g |
| Rosin ester | 2.5 g |
| Isopropanol | 3.5 g |
| ¼ sec. Nitrocellulose | 8.0 g |

Both samples were then immersed for 30 minutes in a 5% aqueous solution of penicillin G and then air dried overnight. The coated samples were then extracted for 18 hours in human plasma at 37° C. They were removed from the plasma, rinsed in running deionized water and then tested for anti-microbial activity as in Example 5. The sample containing nitrocellulose showed a strong zone of inhibition while the sample without nitrocellulose showed no zone of inhibition.

EXAMPLE 8

Example 7 was repeated, except that TDMAC was added to the coating solutions as follows:

| Example 8 | .025 gm TDMAC added |
| --- | --- |
| Example 8A | .075 gm TDMAC added |

Both samples showed a strong zone of inhibition after the 18 hours plasma extraction and appeared to be substantially comparable to Example 7.

EXAMPLE 9

Polyurethane 7 French tubing was coated with the following solution.

| Heparin tridodecylmethylammonium chloride | 0.2 g |
| --- | --- |
| Isopropanol | 2.6 g |
| Methylethylketone | 2.5 g |
| 7A Solution | 0.7 g |

This coated sample was tested for clotting and did not clot. It was very resistant to removal in hot running water.

EXAMPLE 10

Polyurethane 7 French tubing was coated with a solution containing the following ingredients and dried at ambient temperature for 60 minutes:

| Methylethylketone | 5.3 g |
| --- | --- |
| Heparin-benzalkonium chloride | 0.31 g |
| Isopropanol | 3.4 g |
| Acrylic resin | 0.2 g |
| Rosin ester | 0.2 g |
| Tridodecylmethylammonium chloride | 0.4 g |
| Xylene | 0.14 g |
| Butanol | 0.05 g |

Samples were then extracted in plasma at 37° C. for 4, 24 and 120 hours and compared to uncoated polyurethane tubing for anti-clotting activity. The results were as follows:

| Sample | Clotting Time |
| --- | --- |
| Uncoated control | 9 minutes |
| Above sample, without extraction in plasma | Did Not Clot |
| Above sample, after 4 hours extraction in plasma | Did Not Clot |
| Above sample, after 24 hours extraction in plasma | Did Not Clot |
| Above sample, after 120 hours extraction in plasma | Did Not Clot |

The above coated sample was resistant to removal by hot running water.

EXAMPLE 11

Polyurethane 7 French tubing was coated with a solution containing the following ingredients and dried 15 minutes at 75° C.:

| Methylethylketone | 5.6 g |
| --- | --- |
| Heparin-benzalkonium chloride | 0.33 g |
| Isopropanol | 3.5 g |
| Polyurethane resin | 0.24 g |
| Polyisocyanate resin | 0.19 g |
| Ethyl acetate | 0.19 g |

Samples were extracted in plasma at 37° C. for 72 hours and then tested for anti-clotting properties. A sample of polyurethane tubing which was coated with heparin-benzalkonium chloride (1.8% w/v in isopropanol) was also extracted in plasma at 37° C. for 72 hours for comparison. The following results were obtained:

| Sample | Clotting Time |
| --- | --- |
| Uncoated control | 13 minutes |
| Above sample, after 72 hours extraction in plasma | Did Not Clot |
| Sample coated with heparin-benzalkonium chloride in isopropanol, after 72 hours extraction in plasma | 7 minutes |

The above coating was also resistant to removal by hot running water.

EXAMPLE 12

Polyurethane 7 French tubing was coated with a solution containing the following ingredients and dried for 20 minutes at 70° C.

| Methylethylketone | 5.9 g |
| --- | --- |
| Heparin-benzalkonium chloride | 0.32 g |
| Isopropanol | 3.5 g |
| Polyurethane resin | 0.14 g |
| Polyisoyanate resin | 0.07 g |
| Ethylacetate | 0.07 g |

Samples were then extracted in human plasma at 37° C. for 3, 24, and 48 hours and then tested for anti-clotting properties. The following results were obtained:

| Sample | Clotting Time |
| --- | --- |
| Uncoated control | 8 minutes |
| Above sample, after 3 hours extraction in plasma | Did Not Clot |
| Above sample, after 24 hours extraction in plasma | Did Not Clot |
| Above sample, after 48 hours extraction in plasma | 9 minutes |

EXAMPLE 13

Polyurethane 7 French tubing was coated with a solution containing the following ingredients and dried for 20 minutes at 70° C.

| | |
|---|---|
| Methylethylketone | 6.1 g |
| Heparin-benzalkonium chloride | 0.32 g |
| Isopropanol | 3.5 g |
| Polyurethane resin | 0.07 g |
| Polyisoyanate resin | 0.04 g |
| Ethylacetate | 0.04 g |

Coated tubing was then extracted in plasma for 3 and 24 hours and then tested for anti-clotting behavior. The following results were obtained:

| Sample | Clotting Time |
|---|---|
| Uncoated control | 8 minutes |
| Above sample, after 3 hours extraction in plasma | Did Not Clot |
| Above sample, after 24 hours extraction in plasma | 9 minutes |

EXAMPLE 14

Polyurethane 7 French tubing was coated with a solution containing the following ingredients and dried for 20 hours at 55° C.

| | |
|---|---|
| Heparin tridodecylmethylammonium chloride | 0.32 g |
| Dimethylacetamide | 6.2 g |
| Toluene | 2.0 g |
| Petroleum ether | 1.5 g |

The coated tubing was extracted in human plasma at 37° C. for 1, 2, 3 and 6 days and then tested for anti-clotting properties.

| Sample | Clotting Time |
|---|---|
| Uncoated sample | 10 minutes |
| Above sample, after 1 day extraction in plasma | Did Not Clot |
| Above sample, after 2 days extraction in plasma | Did Not Clot |
| Above sample, after 3 days extraction in plasma | Did Not Clot |
| Above sample, after 6 days extraction in plasma | Did Not Clot |

The preceding examples, together with controls, show clearly that heparin-quaternary ammonium compounds that are not polymeric can be made more resistant to removal or deactivation in various body fluids such as whole blood or plasma (including human) by mixing with appropriate water-insoluble polymers. Coatings made from normal heparin-quaternary ammonium compounds by themselves using solvents that do not cause mixing with the substrate, such as heparin-benzalkonium chloride, or heparin tridodecylmethylammonium chloride show little anti-thrombogenicity after soaking in human plasma for only a few hours. The heparin-TDMAC compound continues to show anti-thrombogenicity somewhat longer than the benzalkonium chloride compound, but both exhibit almost no anti-thrombogenicity after soaking in human plasma for a few hours. The incorporation of water-insoluble polymers according to the present invention, and as shown in the examples, greatly extends the time for which coating samples can be soaked in human plasma and still show substantially levels of anti-thrombogenicity. For instance, some samples were found to show anti-thrombogenicity even after soaking in human plasma for 28 days.

On the other hand, when quarternary ammonium polymers are reacted with heparin, the coating remains on the surface even after long periods of soaking in body fluids such as human plasma, but the anti-thrombogenicity is not as strong either before soaking or after soaking for up to 28 days in human plasma, as in the samples made according to this invention. It is further noted that by water-insoluble polymers we are implying that they are water-insoluble after a film is cast and dried, and include water-insoluble polymers that may be hydrophilic, but nevertheless cause the heparin-quaternary ammonium compounds to remain anti-thrombogenic after prolonged soaking in body fluids.

Other modifications and ramifications of the present invention would appear to those skilled in the art upon a reading of this disclosure. These are intended to be included within the scope of this invention.

What is claimed is:

1. An anti-thrombogenic composition comprising heparin reacted with a quaternary ammonium component mixed with a water-insoluble polymer, whereby said composition exhibits a degree of anti-thrombogenic characteristics for a relatively long period of time, and a resistance to removal or deactivation in human or animal body fluids when coated on a substrate.

2. The composition of claim 1 in which the quaternary ammonium is also reacted with an antibiotic which is capable of being gradually released to provide effective anti-microbial action over a relatively long period of time.

3. The composition of claim 2 in which the antibiotic agent is negatively charged and is selected from the group consisting of penicillin, ticarcillin, cefotoxin cephalosporins, oxacillin, and carbenicillin.

4. The composition of claim 1 in which the polymer is at least one selected from the group consisting of cellulose esters, polyurethane resins, acrylic polymers, condensation polymers, and polyisocyanates.

5. The composition of claim 1 in which the heparin-quaternary compound is present in a concentration of about 0.5% to 99.5% by weight with the balance comprising the water-insoluble polymer.

6. The composition of claim 1 which the quaternary ammonium compounds that are reacted by heparin include at least one of benzalkonium chloride, tridodecylmethylammonium chloride, cetylpyridinium chloride, benzyldimethylstearylammonium chloride, and benzylcetyldimethylammonium chloride.

7. An anti-thrombogenic composition comprising heparin reacted with a quaternary ammonium component mixed with a water-insoluble polymer which consists of at least one selected from the group consisting of water-insoluble cellulose polymers comprising nitrocellulose, cellulose acetate butyrate or cellulose acetate propionate; acrylic resin; polyurethane resin; polyisocyanate resin; and condensation polymers, whereby said composition exhibits a degree of anti-thrombogenic characteristics for a relatively long period of time, and a resistance to removal or deactivation in human or animal fluids when coated on a substrate.

8. The composition of claim 7 in which the heparin compound comprises heparin benzalkonium chloride.

9. The composition of claim 7 in which the quaternary ammonium compounds that are reacted with heparin include at least one selected from the group consisting of cetylpyridinium chloride, tridodecylmethylammonium chloride, benzyldimethylstearylammonium chloride, and benzylcetyldimethylammonium chloride.

10. The composition of claim 7 in which the quaternary ammonium is also reacted with an antibiotic which is capable of being gradually released to provide effective anti-microbial action over a relatively long period of time.

11. The composition of claim 7 in which the heparin-quaternary ammonium compound is present in a concentration of at least 0.5% by weight of the coating.

* * * * *